United States Patent [19]

Manska

[11] Patent Number: 5,135,026
[45] Date of Patent: * Aug. 4, 1992

[54] MEDICAL VALVE HAVING FLUID FLOW INDICIA

[76] Inventor: Wayne E. Manska, 1921 Kellogg Dr., Anaheim, Calif. 92807

[*] Notice: The portion of the term of this patent subsequent to Nov. 6, 2007 has been disclaimed.

[21] Appl. No.: 394,877

[22] Filed: Aug. 16, 1989

[51] Int. Cl.⁵ .................. F16K 37/00; F16K 11/085
[52] U.S. Cl. .................. 137/555; 137/556; 137/557; 137/625.47; 604/248
[58] Field of Search .................. 137/1, 555, 556, 556.3, 137/556.6, 557, 625.47; 604/32, 248

[56] References Cited

U.S. PATENT DOCUMENTS

| | | | |
|---|---|---|---|
| D. 271,421 | 11/1983 | Fetterman | 604/248 X |
| 1,383,231 | 6/1921 | Nelson | 137/555 |
| 2,485,842 | 10/1949 | Pennington . | |
| 2,991,804 | 7/1961 | Merkle . | |
| 3,012,752 | 12/1961 | Buck | 251/904 X |
| 3,276,472 | 10/1966 | Jinkens | 137/556 |
| 3,344,785 | 10/1967 | Hamilton | 137/625.47 X |
| 3,481,367 | 12/1969 | Deuschle . | |
| 3,485,265 | 12/1969 | Buono | 137/556.6 |
| 3,581,733 | 6/1971 | Grandjean . | |
| 3,668,935 | 6/1972 | Coelho et al. | 73/863.72 |
| 3,690,312 | 9/1972 | Leibinshon . | |
| 3,750,704 | 8/1973 | Burke et al. | 137/625.47 |
| 3,759,295 | 9/1973 | Dence . | |
| 3,774,604 | 11/1973 | Danielsson | 137/625.47 X |
| 3,780,736 | 12/1973 | Chen . | |
| 3,788,602 | 1/1974 | Kitzie | 251/904 X |
| 3,834,372 | 9/1974 | Turney . | |
| 3,945,603 | 3/1976 | Fraser . | |
| 3,957,082 | 5/1976 | Fuson et al. | 251/904 X |
| 4,146,055 | 3/1979 | Ryder et al. | 137/625.47 X |
| 4,177,835 | 12/1979 | Paley | 137/625.47 X |
| 4,187,882 | 2/1980 | Watson . | |
| 4,207,923 | 6/1980 | Giurtino | 137/625.47 |
| 4,219,021 | 8/1980 | Fink | 604/248 X |
| 4,462,372 | 7/1984 | Jackson . | |
| 4,517,844 | 5/1985 | Powell . | |
| 4,545,389 | 10/1985 | Schaberg . | |
| 4,566,480 | 1/1986 | Parham | 137/625.47 X |
| 4,593,717 | 6/1986 | Levasseur | 137/556.6 |
| 4,608,996 | 9/1986 | Brown . | |
| 4,653,537 | 3/1987 | Voith . | |
| 4,673,386 | 6/1987 | Gordon . | |
| 4,763,648 | 8/1988 | Wyatt . | |
| 4,789,000 | 12/1988 | Aslanian | 251/904 X |
| 4,790,193 | 12/1988 | Moriuchi et al. | 137/625.47 X |
| 4,802,506 | 2/1989 | Aslanian . | |
| 4,890,817 | 1/1990 | Uri | 251/904 X |
| 4,904,245 | 2/1990 | Chen et al. | 137/625.47 X |
| 4,967,797 | 11/1990 | Manska | 137/625.47 |
| 5,046,528 | 9/1991 | Manska | 137/556 |

FOREIGN PATENT DOCUMENTS

| | | |
|---|---|---|
| 289676 | 1/1916 | Fed. Rep. of Germany . |
| 2313363 | 9/1974 | Fed. Rep. of Germany . |
| 3319625 | 12/1984 | Fed. Rep. of Germany . |
| 16593 | of 1899 | United Kingdom . |
| 1554712 | 10/1979 | United Kingdom . |

OTHER PUBLICATIONS

Brochure—Utah Medical Products, Inc., Delta-Plex, Pricing, Jun. 3, 1988 (15 pages).

Primary Examiner—Gerald A. Michalsky
Attorney, Agent, or Firm—Knobbe, Martens, Olson & Bear

[57] ABSTRACT

A medical valve comprises a rotatable member having a fluid flow path formed by a passageway. Flow path indicia on a surface of the rotatable member follows a path along the surface which substantially replicates the fluid flow path of the passage so as to indicate the orientation of the fluid flow path.

25 Claims, 2 Drawing Sheets

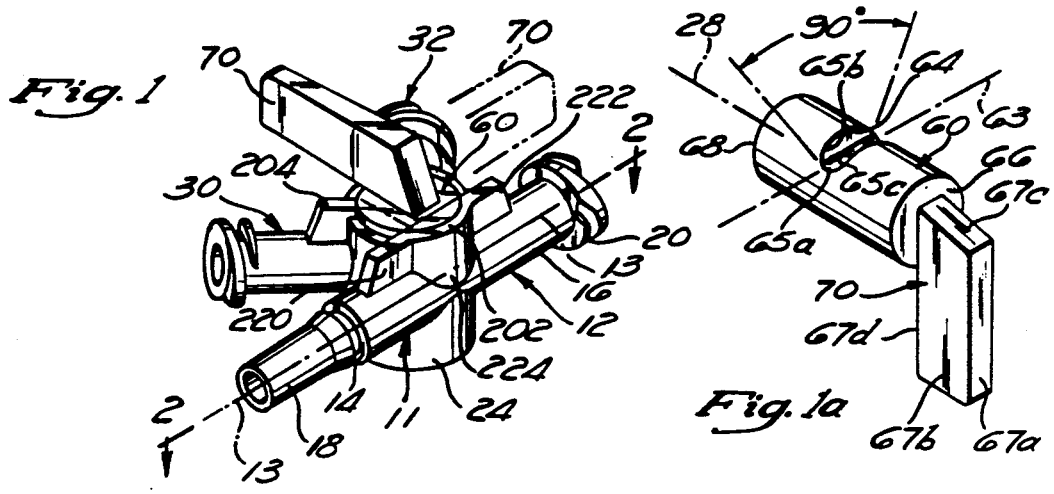
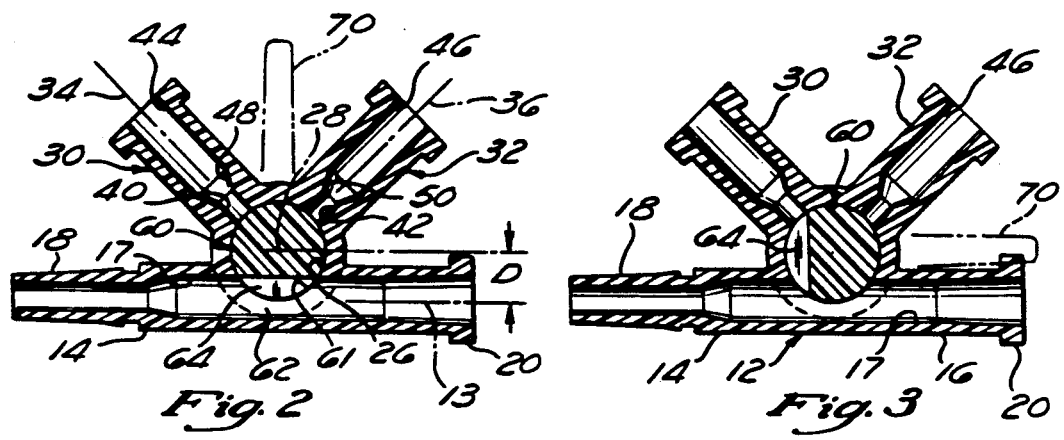
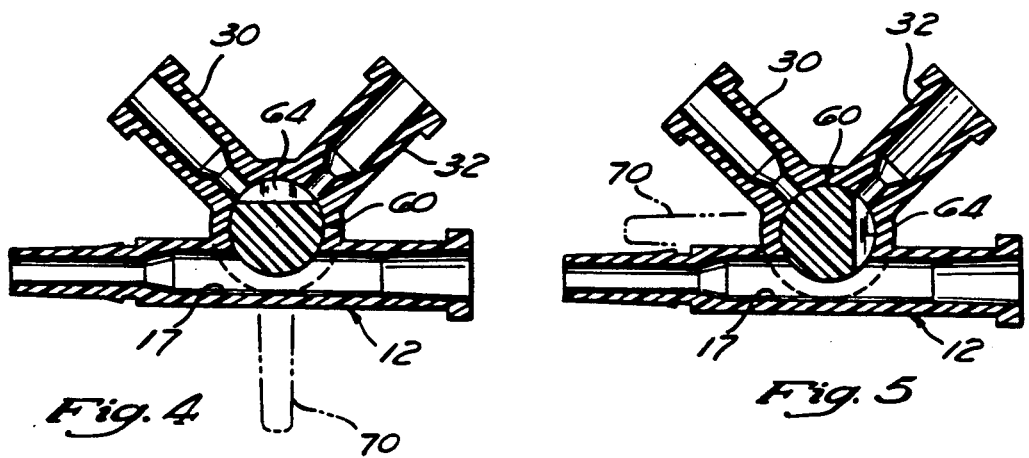

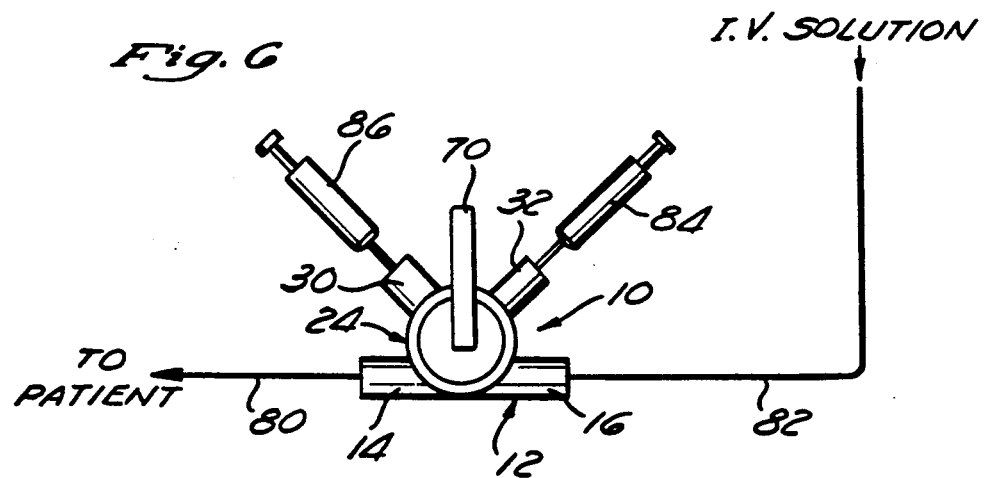
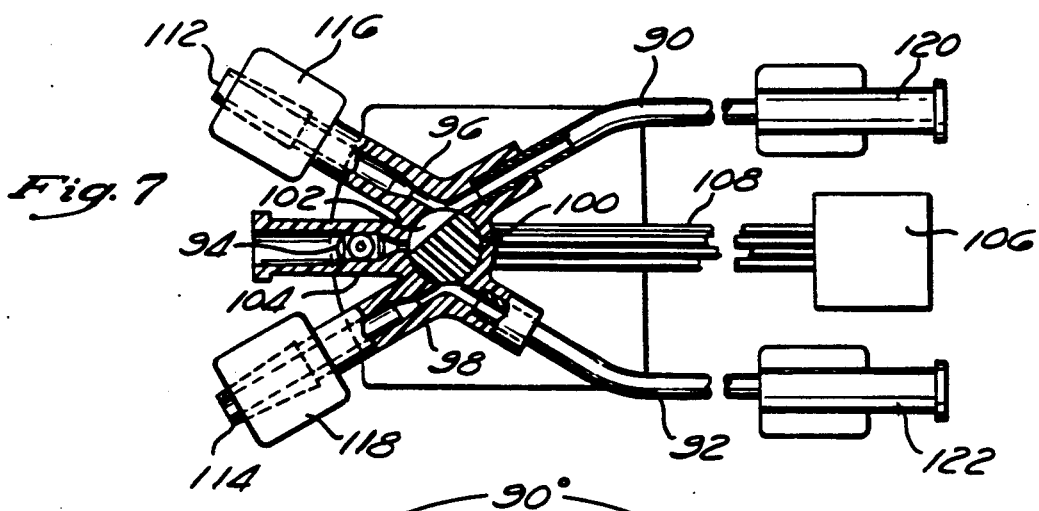
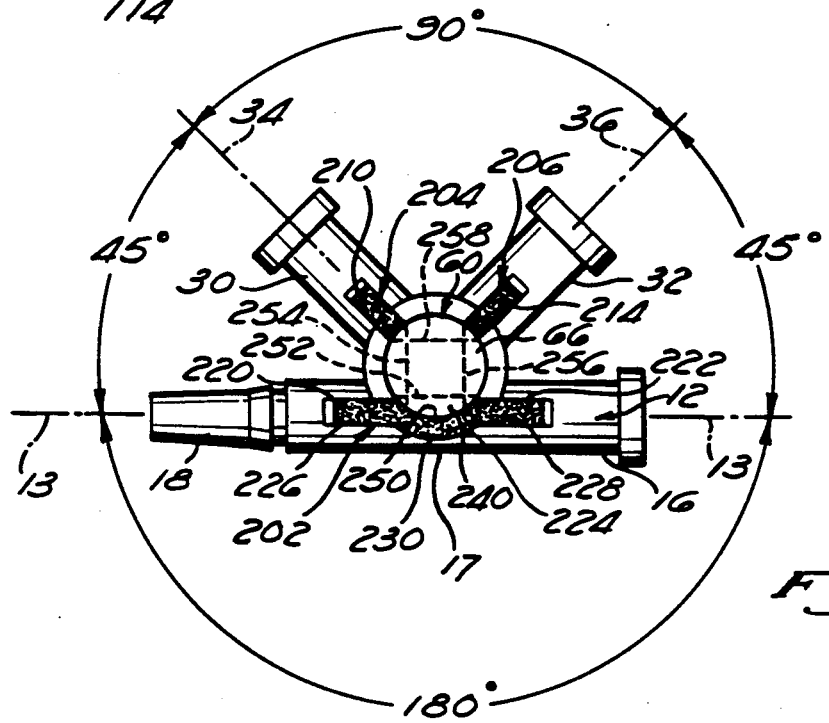

5,135,026

MEDICAL VALVE HAVING FLUID FLOW INDICIA

BACKGROUND OF THE INVENTION

The present invention relates generally to valves, and particularly to medical valves.

Valves are commonly used to control fluid flow between multiple fluid flow openings. Prior art medical valves typically utilize handles formed as arrows, or handles having arrows or similar indicia printed thereon to designate fluid connections. However, such indicia can be difficult to properly interpret and may be confusing or at least ambiguous in defining fluid flow paths. Accordingly, there is a need in the art for a medical valve which provides a highly visible map of the fluid path connections of the valve.

SUMMARY OF THE INVENTION

The present invention comprises a valve having a valve body which mounts a rotatable member having a passageway. The valve body includes at least first and second fluid flow openings adjacent to the rotatable member. By way of example, one of the fluid flow openings may be a tapping port and the other fluid flow opening may comprise a port of a throughput tube. The rotatable member has at least two positions, one of which orients the passage for fluid communication between the firs&: and second fluid flow openings, and the other of the positions orients the passageway to prevent fluid communication between the first and second fluid flow openings. Flow path indicia on the rotatable member follows a continuous path along a surface of the rotatable member and replicates the fluid flow path of the passage so as to indicate the orientation and extent of the fluid flow path. In the preferred embodiment, the valve body includes a third fluid flow opening and the other of the positions orients the passageway for fluid communication between the first and third fluid flow openings. By way of example, the third fluid flow opening may comprise another port in the throughput tube. Indicia on the valve body designate the locations of the first, second and third fluid flow openings, and indicia on the rotatable member designate the fluid flow path formed by the passageway to indicate whether the rotatable member is oriented for fluid communication between the first and second openings or between the first and third openings. The fluid flow openings are preferably disposed relative to the rotatable member such that the indicia on the rotatable member (1) matches the indicia designating the first and second fluid flow openings when the passageway is oriented for fluid communication between the first and second fluid flow openings, and (2) matches the indicia designating the first and third fluid flow openings when the passageway is oriented for fluid communication between the first and third fluid flow openings. The indicia on the rotatable member and the indicia on the valve body designating the openings lie substantially in a common plane in the preferred embodiment.

In the preferred embodiment, the valve comprises a tap valve and the valve body comprises a throughput tube and a housing. Preferably, the housing and throughput tube are integrally formed as a single unit. The throughput tube provides a fluid flow channel between first and second ends. The rotatable valve member is mounted in fluid communication with the fluid flow channel at a predetermined location, such that an exterior surface of the rotatable member is laterally spaced from an interior wall of the fluid flow channel at the predetermined location to permit fluid flow therebetween. The rotatable member is mounted along an axis of rotation which is offset from the longitudinal axis of the throughput tube, and the rotatable valve member has a generally circular cross section.

The housing further includes a tapping port having an end which terminates at the rotatable member. The rotatable member has multiple positions, including a first position for orienting a passage to enable fluid flow between the throughput tube and the tapping port without closing off the fluid flow channel at the predetermined location. The rotatable member also has a second position which seals the tapping port to disable fluid flow between the throughput tube and the tapping port without closing off the fluid flow channel at the predetermined location.

The invention also comprises a method of selectively tapping fluid from a throughput tube using a rotatable member. The method includes the step of using flow path indicia which replicates a fluid passage of the rotatable member to determine the orientation of the passage. The rotatable member is then rotated to orient the indicia to designate fluid communication between the throughput tube and a tapping port. Fluid flow is then provided to the tapping port without disabling the fluid flow through the tube. The rotatable member is additionally rotated to orient the indica such that the passage is oriented for fluid communication exclusively with the throughput tube, and a portion of the fluid flow in the throughput tube is passed through the passage, without closing off the fluid flow through the tube, to prevent stagnation of the fluid in the passage. Such method is useful, for example, in obtaining blood samples from an I.V. line attached to a patient.

DESCRIPTION OF THE DRAWINGS

These and other features of the present invention may be more fully understood through reference to the drawings in which:

FIG. 1 is a perspective view of a tap valve having the fluid flow indicia of the present invention;

FIG. 1a is a perspective view of the rotatable member and handle, showing the groove in the rotatable member which provides a selectively oriented passage between ports of the valve;

FIG. 2 is a cross-sectional view, taken along the lines 2—2 of FIG. 1, showing the rotatable member partially intercepting the fluid flow channel and further showing the rotatable member in an "idle" position which prevents fluid communication between the throughput tube and either of the tapping ports;

FIG. 3 is a cross-sectional view, taken along the same lines as FIG. 2, showing the rotatable member oriented to provide fluid communication between the throughput tube and one of the tapping ports;

FIG. 4 is a cross-sectional view, taken along the same lines as FIG. 2, showing the rotatable member oriented for fluid communication between the two tapping ports;

FIG. 5 is a cross-sectional view, taken along the same lines as FIG. 2, showing the rotatable member oriented for fluid communication between the throughput tube and the other of the tapping ports;

FIG. 6 is a schematic drawing illustrating use of the tap valve to obtain blood samples from a patient;

FIG. 7 is a plan view in partial cross section showing an alternative embodiment of the tap valve of the present invention in which the tap valve provides fluid communication between either of two lines and a pressure transducer; and FIG. 8 is a plan view of the tap valve of FIG. 1 showing indicia for designating fluid flow paths through the tap valve.

DETAILED DESCRIPTION OF THE PREFERRED EMBODIMENT

As shown in FIGS. 1-5, a tap valve 10 comprises a valve body 11 having throughput tube 12 with a central longitudinal axis 13. The tube 12 includes ends 14, 16 which form inlet or outlet ports, and a fluid flow channel 17 for carrying fluid in either direction between the ports 14, 16. Connectors 18, 20 are provided at the ports 14, 16, respectively, to permit connection of the throughput tube 12 to, for example, an I.V. line. In the preferred embodiment, the connectors 18, 20 are formed as male and female luer fittings, respectively.

The valve body 11 additionally comprises a housing 24 on which the throughput tube 12 is mounted. In the preferred embodiment, the housing 24 is integrally formed with the throughput tube 12 such that the valve body 11 is a single unitary structure. The housing 24 comprises a cylindrical member having a longitudinal bore 26 (FIG. 2) therein. The bore 26 has a central longitudinal axis 28 which is (a) orthogonal to the central longitudinal axis 13 of the throughput tube 12 and (b) laterally displaced therefrom by a distance D. In the preferred embodiment, the distance D is greater than the radius of the fluid flow channel 17, and is approximately equal to the radius of the bore 26.

The housing 24 includes two ports 30, 32 comprising tubes having central longitudinal axes 34, 36, respectively, which pass through the central longitudinal axis 28 of the bore 26 in a direction orthogonal to the axis 28. In the preferred embodiment, the axes 34, 36 are disposed at approximately 45° relative to the axis 13. The ports 30, 32 are formed as female luer fittings having terminal end openings 40, 42, respectively, which provide fluid flow openings at the bore 26 for fluid communication therebetween, and distal end openings 44, 46, respectively, which are sized to receive the output end of a syringe. The distal end openings 44, 46 are enlarged relative to the terminal end openings 40, 42, respectively. Tapered wall portions 48, 50, respectively, provide transitions between the distal ends and terminal ends. Although the ports 30, 32 of the preferred embodiment are configured as luer fittings which accept syringes, it will be understood that alternative configurations could be used for connecting other devices or tubes.

A rotatable core member 60 having a central longitudinal axis coincident the with the axis 28 is mounted in the bore 26 for rotation about the axis 28. The member 60 is generally cylindrical and has a diameter substantially equal to the inside diameter of the bore 26 so as to fluidly seal the rotatable member 60 against the interior sides of the bore 26. The radius of the rotatable member 60 is approximately equal to the distance D, such that the rotatable member projects through an opening 61 in the inner side wall of the throughput tube 12 and into the fluid flow channel 17 formed by the throughput tube 12. The rotatable member only partially intercepts the fluid flow channel 17 so as to allow continuous fluid flow along the axis 13 through an opening or passageway 62 between the exterior surface of the rotatable member 60 and an interior surface of the throughput tube 12.

As best seen in FIG. 1a, the rotatable member 60 includes a groove 64 on one side thereof, which extends through about 90° of circumference of the rotatable member 60, and is disposed between end surfaces 66, 68 of the cylindrical rotatable member 60 such that, when mounted in the bore 26, the groove 64 is aligned with the fluid flow channel 17 of the throughput tube 12. In other words, the groove 64 lies in a plane defined by the opening 61 in the tube 12 and the terminal end openings 40, 42 of the ports 30, 32. The groove 64 has a longitudinal axis 63 which is orthogonal to and spaced from the axis of rotation 28. The length of the groove 64 is approximately equal to the length of the opening 61 in the throughput tube 12 in which the rotatable member 60 is mounted, and the width of the groove 64 is approximately equal to the diameter of the terminal end openings 40, 42 of the ports 30, 32, respectively. The depth of the groove 64 at the center thereof (i.e., at the midpoint of its length) is approximately equal to the radius of the fluid flow channel 17. The groove 64 comprises a bottom wall 65a and side walls 65b, 65c. The side walls 65b, 65c extend to the exterior surface of the rotatable member 60 such that the groove is open along its length and has the appearance of a notch or cut-out. This configuration permits substantially optimum flow with minimum obstructions between the ports 30, 32 and tube 12.

A handle 70 comprises an elongate bar-shaped member having a top surface 67a, side surfaces 67b, 67c and a bottom surface 67d. The bottom surface 67d is attached to the end surface 66 of the rotatable member 60 such that the surface 66 is substantially beneath the surface 67a. The elongate member 70 has a longitudinal dimension which is preferably oriented to project away from the groove 64 in a direction perpendicular to the axis of rotation 28.

The handle 70 may be used to facilitate rotation of the member 60 and to orient the rotatable member to any of four preferred positions, as shown in FIGS. 2, 3, 4 and 5. When the handle is oriented in the position shown in FIG. 2, the groove 64 is disposed within the fluid flow channel 17. In this "idle" position, the longitudinal axis 63 (FIG. 1a) of the groove 64 is substantially parallel to the longitudinal axis 13 of the throughput tube 12 and thus, fluid flowing through throughput tube 12 will continuously flow along the walls 65 of the groove 64 and thereby flush the interior of the groove 64 to prevent fluid from stagnating therein.

When the handle 70 is rotated 90° to the position shown in FIG. 3, one end of the groove 64 is open to the throughput tube 12, and the other end of the groove 64 is open to the terminal end opening 40 of the tapping port 30. The groove 64 thus provides a passage for fluid communication between the tapping port 30 and the throughput tube 12. The passageway is formed by the surfaces 65 of the groove 64 and an interior surface portion of the bore 26. In this "tapping" position, fluid may be tapped from the throughput line 12 to the port 30, or injected through the port 30 into the throughput line 12.

Rotation of the handle 70 by an additional 90° orients the groove 64 to provide a passage for fluid communication between the tapping ports 30, 32, as shown in FIG. 4. In this position, fluid from one port may be injected into the other port.

Further rotation of the handle 70 by 90° orients the groove 64 to provide a passageway for fluid communication between the tapping port 32 and the throughput tube 12. It will be understood that the valve may be rotated in either a clockwise or counterclockwise direction to achieve the above positions.

The valve 10 is suitable for a variety of applications. One such application involves drawing blood from a patient through an I.V. line connected to a supply of I.V. solution. As shown schematically in FIG. 6, the ends 14, 16 of the throughput tube 12 may be attached to I.V. line segments 80, 82, respectively. Typically, the line segment 82 would be connected to a source of I.V. solution, and the line segment 80 would be connected to deliver such solution into a patient. When the tap valve 10 of the present invention is in its "idle" position, depicted in FIG. 2, the I.V. solution would flow through the segment 82, into the valve 10, through the valve 10 into the segment 80, and through the segment 80 into the patient.

When a blood sample from the patient is desired, the I.V. line 82 is preferably clamped to prevent flow therethrough, and the handle 70 is rotated to the tapping position depicted in FIG. 5 so as to provide fluid communication between the port 16 and the tapping port 32. A syringe 84, connected to the tapping port 32, is used to draw fluid from the throughput line 12 through the tapping port 32. Such drawing of fluid causes blood to be drawn from the patient through the line segment 80. The drawing of blood is continued until undiluted blood from the patient reaches at least the opening 62 in the throughput tube 12. The handle 70 is then rotated to the tapping position shown in FIG. 3 to fluidly connect the throughput tube 12 to the tapping port 30. A second syringe 86 is then used to draw blood from the throughput tube 12 through the tapping port 30 and into the syringe 86 to provide an undiluted blood sample for analysis. Preferably, the handle 70 is then rotated back to the tapping position shown in FIG. 5, and the fluid drawn into the syringe 84 is reinjected into the throughput tube 12 and carried to the patient by the line 80. Finally, the handle 70 may be returned to the "idle" position shown in FIG. 2. In this position, the passage formed by the groove 64 is exposed to flow of I.V. solution through the throughput tube 12, and any blood remaining in the passage 64 will be flushed out by flow of I.V. solution through the throughput tube 12.

FIG. 7 illustrates another embodiment of the tap valve which selectively monitors either of two fluid flow lines 90, 92 with a single sensor 94. In this embodiment, a pair of throughput tubes 96, 98 are disposed on opposite sides of a rotatable member 100 having a groove 102. The sensor 94 is disposed at a port 104, between the throughput tubes 96, 98 such that the groove 102 provides a passage for fluid communication between either the port 104 and the throughput tube 96 or the port 104 and the throughput tube 98. In such manner, a single sensor can be used to monitor either of two lines, thereby eliminating the need for two sensors. In the embodiment disclosed, the sensor 94 comprises a pressure transducer which is connected to electronics 106 by wires 108. The lines 90, 92 are attached to ends of the throughput tubes 96, 98, respectively, by cementing the lines 90, 92 into slip-fit connectors. The other ends of the throughput tubes 96, 98 include male luer fittings 112, 114, respectively, with associated luer nuts 116, 118, respectively. The distal end of the lines 90, 92 include female luer fittings 120, 122.

As shown in FIG. 8, the valve 10 includes indicia for designating the fluid flow paths through the valve for the various handle orientations shown in FIGS. 2-5. In the preferred embodiment, indicia are disposed on raised portions 202, 204, 206, adjacent the periphery of the rotatable member 60. The raised portion 204 comprises an elongate member which is longitudinally aligned with the longitudinal axis 34 of the port 30, and the raised portion 206 comprises an elongate member which is longitudinally aligned with the longitudinal axis 36 of the port 32. The members 204, 206 have corresponding surfaces 210 and 214, both of which are coplanar with the surface 66 of the rotatable member 60. The raised portion 202 includes a pair of elongate members 220, 222 and an arcuate member 224 which extends between the elongate members 220, 222. The arcuate member 224 abuts the peripheral edge of the surface 66 of the rotatable member 60 through 90° of circumference of the rotatable member 60. The elongate members 220, 222 are longitudinally aligned with the longitudinal axis 13 of the throughput tube 12, and are disposed along the end portions 14, 16, respectively of the throughput tube 12. The members 220, 222 and 224 have corresponding surfaces 226, 228 and 230, respectively, all of which are coplanar with the surface 66 of the rotatable member 60. Preferably, all of the surfaces 210, 214, 226, 228 and 230 are colored so as to visually distinguish these surfaces from the remainder of the valve 10.

The surface 66 of the rotatable member 60 comprises fluid path indicia at a location which corresponds to that of the groove 64 (FIG. 1a). In the preferred embodiment, the indicia comprises a colored strip 240, shaped in the form of circular segment, having an arcuate boundary 250 at a peripheral edge of the surface 66, and a chord boundary 252 which lies along a chord of the circle formed by the peripheral edge of the surface 66. The colored strip 240 has approximately the same dimensions and configuration as the side surfaces 65b, 65c forming the groove 64, and extends through 90° of circumference of the rotatable member 60. Thus, the colored strip 240 follows a continuous path on the surface 66 which substantially duplicates the fluid flow path formed by the passage 64 so as to indicate the direction and extent of the fluid flow path. Preferably, the colored strip 240 is of the same color as the surfaces 210, 214, 226, 228 and 230.

The handle 70 extends longitudinally in a direction away from the colored strip 240, as indicated in FIG. 1, so that the handle does not cover or inhibit viewing the colored strip. For clarity of illustration of the indicia, the handle 70 has not been shown in FIG. 8. In the preferred embodiment, the handle 70 projects above the surface 66 such that the bottom surface 67d of the handle 70 is above the surfaces 210, 214, 226, 228 and 230 in order to clear these surfaces and thereby permit rotation of the handle through 360° in a plane of rotation which is perpendicular to the axis of rotation 28 of the rotatable member 60. The plane of rotation of the handle 70 is above the surfaces 66, 210, 214, 226, 228 and 230 such that the fluid path indicia 240 is disposed between the plane of rotation of the handle 70 and the passage 64.

When the handle 70 is oriented in a direction corresponding to the handle position of FIG. 2, the colored strip 240 is disposed adjacent to the arcuate surface 230, as shown in FIG. 8, and blends into the colored surfaces 226, 228, 230 so as to designate the "idle" position. In this position, there is no fluid communication between the throughput tube 12 and either of the tapping ports 30, 32. When the rotatable member 60 is rotated 90° clockwise from the "idle" position, such that the chord boundary 252 coincides with the dotted line 254 in FIG. 8, the passage formed by the groove 64 (FIG. 1a) will be oriented to correspond to that shown in FIG. 3, so as to provide fluid communication between the throughput tube 12 and tapping port 30. In this position, the colored strip 240 will extend between the surface 210 and the surface 226 to designate fluid communication between the tube 12 and port 30. Similarly, when the rotatable member is rotated counterclockwise from the "idle" position by 90°, such that the chord boundary 252 coincides with the dotted line 256 in FIG. 8, the passage 64 will be oriented as shown in FIG. 5, and the colored strip will extend between the surface 228 and the surface 214, thereby indicating fluid communication between the tube 12 and tapping port 32. Finally, when the rotatable member 60 is rotated 180° relative to the "idle" position, such that the chord boundary 252 coincides with the dotted line 258 in FIG. 8, the colored strip 240 will extend between the elongate surfaces 210, 214, thereby indicating fluid communication between the two ports 30, 32.

Accordingly, the indicia on the tube 12, tapping ports 30, 32 and rotatable member 60 cooperate to provide a highly visible map of the passageways within the valve and readily indicate the selectable fluid connections between ports of the valve.

Those skilled in the art will understand that although exemplary uses have been described, the tap valve 10 is a multi-purpose device suitable for a variety of uses, including drug infusion. Further, the fluid path replicating indicia is useful not only in connection with the tap valve disclosed herein, but may be applied to other types of valves having multiple fluid connections such as stopcock valves. Moreover, it is to be understood that the constructions described and illustrated above in connection with the tap valve and fluid path indicia represent only the presently preferred embodiments of the invention, and that various modifications and additions may be made to those embodiments without departing from the scope and spirit of the present invention.

I claim:
1. A valve, comprising:
   a rotatable member having an axis of rotation, said rotatable member including a passageway which defines a fluid flow path;
   a valve body having an opening in which said rotatable member is mounted, said valve body additionally including at least first and second fluid flow openings, said rotatable member having at least two positions, one of said positions orienting said passageway for fluid communication between said first and second fluid flow openings and the other of said positions orienting said passageway to prevent fluid communication between said first and second fluid flow openings;
   flow path indicia on a surface of said rotatable member for designating said fluid flow path formed by said passageway to indicate whether said rotatable member is oriented for fluid communication between said first and second openings, said surface being substantially perpendicular to said axis of rotation, said rotatable member having a peripheral edge disposed proximal to said surface, said indicia on said rotatable member substantially following a substantially continuous path along said surface which substantially replicates the fluid flow path of said passage so as to indicate the orientation of said fluid flow path; and
   indicia on said valve body, disposed laterally outwardly from said peripheral edge of said rotatable member, for designating the locations of said first and second fluid flow openings, said indicia on said valve body being disposed on a portion of said valve body proximal to said peripheral edge, so that said indicia on said valve body is substantially juxtaposed with said indicia on said rotatable member when said passageway is oriented for fluid communication between said first and second fluid flow openings.

2. The valve of claim 1, wherein said valve comprises a tap valve.

3. The valve of claim 2, wherein said first fluid flow opening comprises a tapping port and said second fluid flow opening comprises a port in a throughput tube of said valve body.

4. The valve of claim 1, wherein said valve body comprises a third fluid flow opening, said other of said positions orients said passageway for fluid communication between said first and third fluid flow openings, said flow path indicia designating said fluid flow path to indicate whether said rotatable member is oriented for fluid communication between said first sand third openings.

5. The valve of claim 1, wherein said indicia on said rotatable member and said indicia designating said openings lie in a common plane.

6. The valve of claim 1, additionally comprising a handle mounted on said surface of said rotatable member, said handle mounted on said surface such that said indicia is disposed beneath a top surface of said handle.

7. A tap valve, comprising:
   a throughput tube having a longitudinal axis and including first and second ends, said throughput tube providing a fluid flow channel between said first and second ends;
   a housing for mounting a rotatable valve member which has a generally circular cross-section, said circular cross-section being perpendicular to an axis of rotation of said rotatable member, said housing including a tapping port having an end which terminates at said rotatable member, said rotatable valve member mounted in fluid communication with said fluid flow channel at a predetermined location thereon, and having an exterior surface which is laterally spaced from an interior wall of said fluid flow channel at said predetermined location to permit fluid flow therebetween, said axis of rotation being offset from said longitudinal axis of said throughput tube, said member having multiple positions, including a first position for orienting a passage to permit fluid flow between said throughput tube and said tapping port without closing off said fluid flow channel at said predetermined location, and a second position which seals said tapping port to prevent fluid flow between said throughput tube and said tapping port without closing off said fluid flow channel at said predetermined location; and
   indicia on an external surface of said rotatable member, said indicia disposed relative to said passage to indicate a fluid flow path through said passage.

8. The valve of claim 7, wherein at least a portion of the walls of said passage are defined by a surface on said rotatable member, said surface being in fluid communication with said fluid flow channel when said rotatable member is in said second position.

9. The valve of claim 7, wherein said rotatable member is substantially cylindrical.

10. The valve of claim 7, wherein said throughput tube and said housing are integrally formed as a single unit.

11. The valve of claim 7, additionally comprising a second tapping port, wherein one of said multiple positions of said rotatable member orients said passage to enable fluid flow between said throughput tube and said second tapping port.

12. The valve of claim 11, wherein another of said multiple positions of said rotatable member orients said passage to enable fluid flow between said tapping ports.

13. The valve of claim 7, wherein said tapping port and said throughput tube are angularly displaced from each other by about 45°.

14. The valve of claim 7, additionally comprising a second throughput tube, said rotatable member having a third position for providing fluid communication between said tapping port and said second throughput tube, said valve further including a sensor in communication with said tapping port.

15. The valve of claim 7, wherein at least one of said ends of said throughput tube comprises a luer fitting.

16. The valve of claim 7, wherein said tapping port has an end which comprises a luer fitting.

17. The valve of claim 7, wherein said passage is defined by an exterior surface of said rotatable member and an interior surface of said housing which mounts said rotatable member.

18. The valve of claim 7, wherein said passage is displaced from the axis of rotation of said rotatable member.

19. The valve of claim 7, wherein said axis of rotation is substantially perpendicular to the longitudinal axis of said throughput tube.

20. The valve of claim 19, wherein said external surface is generally perpendicular to said axis of rotation and said indicia is disposed near one edge of said external surface.

21. The valve of claim 20, wherein said rotatable member additionally comprises a handle forming a gripping member which projects away from said one edge of said external surface.

22. The valve of claim 19, wherein said indicia is disposed near the periphery of said rotatable member within an area corresponding to about 90° of circumference.

23. An apparatus, comprising:
a valve body having a throughput path for conducting fluid between an input port and an output port, said valve body also having a tapping port;
a rotatable member having a fluid passage, said rotatable member being mounted on said valve body such that said rotatable member has a first position which orients said passage to provide fluid communication between said throughput path and said tapping port without disabling fluid flow through said throughput path, and has a second position which (i) orients said passage to provide fluid communication exclusively between the input and output ports, (ii) orients said passage such that at least a portion of the fluid flow in said throughput path passes through said passage without disabling said fluid flow through said path, said passage being configured to provide continuous fluid communication between the input and output ports during rotation of said rotatable member between said first and second positions;
flow path indicia which substantially replicates said fluid passage in said rotatable member for determining the orientation of said passage relative to said ports, said flow path indicia being disposed such that said indicia extends between said throughput path and said tapping port, when said rotatable member is in said first position to designate fluid communication therebetween.

24. The apparatus of claim 23, wherein said passage is formed by an exterior surface of said rotatable member.

25. The apparatus of claim 23, wherein the throughput path is formed by a throughput tube and wherein said passage is configured to permit flow of fluid between an exterior surface of the rotatable member and an interior surface of the throughput tube.

* * * * *